(12) United States Patent
Colomb

(10) Patent No.: US 9,050,426 B2
(45) Date of Patent: Jun. 9, 2015

(54) DEVICE FOR DISTRIBUTING A FLUID PRODUCT

(75) Inventor: Arnaud Colomb, Verneuil sur Seine (FR)

(73) Assignee: APTAR FRANCE SAS, Le Neubourg (FR)

( * ) Notice: Subject to any disclaimer, the term of this patent is extended or adjusted under 35 U.S.C. 154(b) by 214 days.

(21) Appl. No.: 12/744,634

(22) PCT Filed: Dec. 2, 2008

(86) PCT No.: PCT/FR2008/052176
§ 371 (c)(1),
(2), (4) Date: May 25, 2010

(87) PCT Pub. No.: WO2009/077697
PCT Pub. Date: Jun. 25, 2009

(65) Prior Publication Data
US 2010/0258120 A1  Oct. 14, 2010

(30) Foreign Application Priority Data

Dec. 3, 2007  (FR) ..................................... 07 59509

(51) Int. Cl.
*A61M 15/00*  (2006.01)
*B65D 83/06*  (2006.01)
(Continued)

(52) U.S. Cl.
CPC ....... *A61M 15/0045* (2013.01); *A61M 15/0091* (2013.01); *A61M 2202/064* (2013.01);
(Continued)

(58) Field of Classification Search
USPC ............ 128/200.11–200.24, 203.12, 203.15, 128/203.19, 203.21, 205.23; 222/32, 33, 222/36, 38, 48, 162, 492.11, 492.13; 116/285, 308, 311, 312, 315, 318; 604/58; 206/459.1, 459.5; 235/116, 235/142, 91 A; 368/124, 198, 254, 269, 77, 368/223, 35, 36, 37, 221; 74/535, 445, 74/571.11, 570.21, 568 T
See application file for complete search history.

(56) References Cited

U.S. PATENT DOCUMENTS 1,476,804 A * 12/1923 De Simone ................. 235/82 R
3,691,755 A *  9/1972 Girard ............................ 368/29
(Continued)

FOREIGN PATENT DOCUMENTS

EP  0949584 A2  10/1999
FR  2721106 A1  12/1995
(Continued)

OTHER PUBLICATIONS

English translation of International Search Report dated Jun. 4, 2009 for International Application No. PCT/FR2008/052176.

*Primary Examiner* — Melanie Hand
*Assistant Examiner* — Ned T Heffner
(74) *Attorney, Agent, or Firm* — Sughrue Mion, PLLC

(57) ABSTRACT

A fluid dispenser device including a body, a dispenser mechanism, and a dose counter. The counter includes a first rotary counter element provided with a first surface including a first indicator, such as digits, and provided with at least one first set of teeth, a second rotary counter element provided with a second surface including a second indicator, such as digits, and provided with at least one second set of teeth, and a movable actuator element. The first counter element includes at least one deformable finger displaceable between a non-deformed position and a deformed position, and that is adapted to co-operate, in its deformed position, with the second set of teeth of the second counter element, so as to cause the second counter element to turn. The body includes a cam that is adapted to deform the deformable finger towards its deformed position.

20 Claims, 12 Drawing Sheets

(51) Int. Cl.
*G06M 1/04* (2006.01)
*G06M 1/24* (2006.01)

(52) U.S. Cl.
CPC ....... *A61M2205/8281* (2013.01); *G06M 1/041* (2013.01); *G06M 1/241* (2013.01); *G06M 1/045* (2013.01); *A61M 15/0008* (2014.02); *A61M 15/0026* (2014.02); *A61M 15/0036* (2014.02); *A61M 15/004* (2014.02); *A61M 15/0041* (2014.02); *A61M 15/0051* (2014.02); *A61M 15/0075* (2014.02)

(56) References Cited

U.S. PATENT DOCUMENTS

| | | | |
|---|---|---|---|
| 5,287,397 A * | 2/1994 | Dumsha | 378/162 |
| 5,564,414 A * | 10/1996 | Walker et al. | 128/200.23 |
| 6,234,168 B1 | 5/2001 | Bruna | |
| 7,100,530 B2 * | 9/2006 | Lu | 116/307 |
| 2004/0149772 A1 * | 8/2004 | Ouyang | 222/36 |
| 2004/0211420 A1 * | 10/2004 | Minshull et al. | 128/203.15 |
| 2006/0150971 A1 * | 7/2006 | Lee et al. | 128/203.15 |
| 2006/0151524 A1 * | 7/2006 | Stradella et al. | 222/23 |
| 2007/0267015 A1 * | 11/2007 | Thoemmes et al. | 128/203.12 |

FOREIGN PATENT DOCUMENTS

| | | |
|---|---|---|
| FR | 2799858 A1 | 4/2001 |
| WO | 01/31578 A1 | 5/2001 |
| WO | 2005/079727 A2 | 9/2005 |
| WO | WO 2005079727 A2 * | 9/2005 |
| WO | 2006/079751 A1 | 8/2006 |
| WO | WO 2006079746 A1 * | 8/2006 |

* cited by examiner

DEVICE FOR DISTRIBUTING A FLUID PRODUCT

CROSS REFERENCE TO RELATED APPLICATION

This application is a National Stage of International Application No. PCT/FR2008/052176 filed Dec. 2, 2008, claiming priority based on French Patent Application No. 0759509, filed Dec. 3, 2007, the contents of all of which are incorporated herein by reference in their entirety.

The present invention relates to a fluid dispenser device, and more particularly to a dry-powder inhaler.

Dry-powder inhalers are well known in the prior art. Various types exist. A first type of inhaler contains a reservoir receiving many doses of powder, the inhaler being provided with metering means making it possible, on each actuation, to remove one dose of said powder from the reservoir, so as to bring said dose into an expulsion duct in order to be dispensed to the user. Another type of inhaler consists in packaging the doses of powder in individual predosed reservoirs, then in opening one of the reservoirs each time the inhaler is actuated. That implementation seals the powder more effectively since each dose is opened only when it is about to be expelled. In order to make such individual reservoirs, various techniques have already been proposed, such as an elongate blister strip or blisters disposed on a rotary circular disk. Inhalers including individual reservoirs, such as capsules, that are loaded into the inhaler just before said reservoir is used are also described in the prior art. The advantage of such devices is that it is not necessary to store all of the doses inside the appliance, such that said appliance can be compact. Obviously however, the inhaler is more difficult to use, since the user is obliged to load a capsule into the inhaler before each use. All existing types of inhalers, including those described above, present both advantages and drawbacks associated with their structures and with their types of operation. Thus, with certain inhalers, there is the problem of accuracy and of reproducibility for the dose on each actuation. In addition, the effectiveness of the dispensing, i.e. the fraction of the dose that effectively penetrates into the user's lungs in order to have a beneficial therapeutic effect, is also a problem that exists with a certain number of inhalers. A solution for solving that specific problem has been to synchronize the expulsion of the dose with the inhalation of the patient. Once again, that can create drawbacks, in particular in that type of device, the dose is generally loaded into an expulsion duct before inhalation, then expulsion is synchronized with inhalation. That means that if the user drops, shakes, or manipulates the inhaler in an undesirable or inappropriate manner between the moment when the user loads the dose (either from a multidose reservoir or from an individual reservoir) and the moment when the user inhales, then the user risks losing all or part of the dose, with said dose possibly being spread about inside the appliance. In that event, there can exist a high risk of overdosing the next time the device is used. The user who realizes that the dose is not complete will load a new dose into the appliance, and while the new dose is being inhaled, a fraction of the previous dose that was lost in the appliance could thus be expelled at the same time as the new dose, thereby causing an overdose. In the treatments envisaged, such overdosing can be very harmful, and the authorities in all countries are issuing ever-stricter requirements to limit the risk of overdosing as much as possible. With regard to opening the individual reservoirs, it has been proposed to peel off or to unstick the closure layer. That presents the drawback of difficulty in controlling the forces to be applied in order to guarantee complete opening, without running the risk of opening the next reservoir, particularly if the opening means need to be actuated by inhalation. In a variant, it has been proposed to perforate the closure layer or wall. That can present the drawback that the cut wall-portions risk retaining a fraction of the dose inside the reservoir, so that metering accuracy and reproducibility are therefore not guaranteed. In addition, it is known to use a dose counter or indicator for informing the user about the number of doses that have been dispensed or that remain to be dispensed. A conventional drawback with such counters is that either they are very bulky, correspondingly increasing the size of the inhaler itself, or the display is very small and often difficult to read, in particular for the elderly. In particular, this is true for counters for counting a high number of doses, e.g. 60 doses.

An object of the present invention is to provide a fluid dispenser device, in particular a dry-powder inhaler, that does not have the above-mentioned drawbacks.

In particular, an object of the present invention is to provide a device that is simple and inexpensive to manufacture and to assemble, that is reliable in use, guaranteeing metering accuracy and metering reproducibility on each actuation, providing an optimum yield with regard to the effectiveness of the treatment, by making it possible to dispense a substantial fraction of the dose to the zones to be treated, in particular the lungs, avoiding, in safe and effective manner, any risk of overdosing, and that is as compact as possible, while guaranteeing sealing and absolute integrity of all of the doses up to their expulsion.

Another object of the present invention is to provide a device that avoids any risk of under-dosing, with the reservoir being opened, the dose being expelled, and the emitted dose being counted only in the event of the user inhaling. In addition, an object of the present invention is to avoid any risk of doses being lost in the absence of any inhalation, even if the user manipulates the device.

Another object of the present invention is to provide a device that makes it possible to count the number of doses that have been emitted or that remain to be emitted and that is of reasonable size, while proposing a display that can easily be read by the users.

Another object of the present invention is to provide a device for counting the number of doses that have been emitted or that remain to be emitted and that is actuated at the time each dose is expelled, so as to guarantee that it counts doses that have effectively been dispensed.

The present invention thus provides a fluid dispenser device according to claim 1.

Advantageous embodiments are described in the dependent claims.

These characteristics and advantages and others of the present invention appear more clearly from the following detailed description of several embodiments and variants thereof, given by way of non-limiting example, and with reference to the accompanying drawings, and in which.

Figure 1:
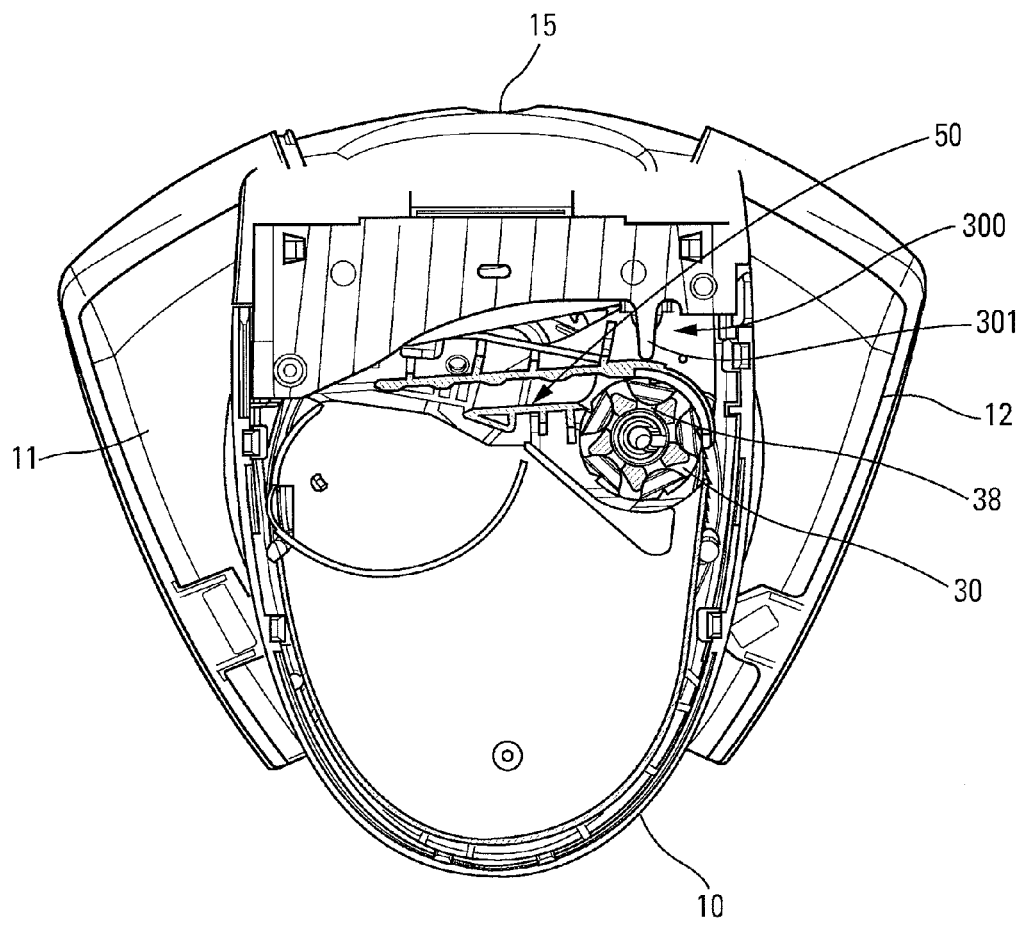
FIG. 1 is a diagrammatic view partially in section of a variant of a fluid dispenser device, in its cocked position, shown before inhalation.

The present invention preferably relates to a dry-powder inhaler. Various variants are shown in the figures, with it being understood that the characteristics shown in the figures could be combined together in any appropriate manner. The drawings are therefore non-limiting. In addition, numerous characteristics of the inhaler could thus be implemented in order to dispense liquid instead of powder. The inhaler comprises a central body 10 on which there are slidably mounted two lateral elements or wings 11, 12 that form a cover when the device is closed and that are adapted to be moved apart in order to open the device and thus cock, stress, or spring-load the device as described below. The body 10 can be approximately rounded in shape at its bottom portion, and relatively flat at its top portion, as shown in particular in FIG. 1, but it could be of any other appropriate shape. The body 10 includes a dispenser and inhaler orifice 15 through which the user inhales while the device is being actuated. The two cover-forming lateral portions 11, 12 can be opened by pivoting about a common pivot axis, but any other opening means can be envisaged for opening the device. Alternatively, it is possible to provide only one cover element that is movable relative to the body, instead of the two shown in particular in FIG. 1.

The body advantageously includes a window 19 through which the count of the doses that have been dispensed or that remain to be dispensed can be displayed in visible manner for the user. By way of example, the window can be provided on or close to the pivot axis of the cover-forming cover elements 11, 12, but it could be in another location. A substrate 20 of individual reservoirs 21 can be provided inside the body. The reservoirs are advantageously of the blister type, and the reservoir substrate is preferably a flexible elongate strip on which the blisters are disposed one behind another, in any appropriate number, in known manner. The blister strip may advantageously be constituted by a base layer or wall that forms cavities receiving the doses of powder, and by a closure layer or wall that covers each of said blisters in sealed manner. The blister strip can be rolled-up inside the body, and first displacement means 30 for displacing the strip are provided for progressively unrolling the blister strip and for bringing a respective blister or individual reservoir into a dispensing position each time the device is actuated. When an individual reservoir has been emptied by inhalation, the strip portion that includes said empty reservoirs is advantageously adapted to be rolled-up at another location of said body 10.

Reservoir-opening means 80 are provided in, or secured to, the body 10, the opening means comprising perforator and/or cutter means for perforating or cutting the closure layer of the blisters. The opening means are shown in diagrammatic manner only in the figures.

Movable support means 50 are adapted to support at least the reservoir that is to be opened during the next inhalation. The movable support means 50 forming second displacement means that are adapted to displace the reservoir to be emptied against said opening means of the device during actuation. Advantageously, the movable support means 50 are urged directly or indirectly by stressing means 800 comprising an elastically-deformable stressing element 51, such as a spring, a rod, or any other equivalent resilient element, said stressing element being prestressed in particular while the device is being opened. Advantageously, the movable support means 50 are displaceable between a first position (a non-dispensing position) and a second position (a dispensing position) that is the position for opening the reservoir and thus the inhalation position.

The movable support means 50 advantageously comprise a substantially rigid part, such as a rod, that is hinged relative to said body 10. A guide or indexer wheel 30 that is fastened in rotary manner on said movable support means 50 receives and guides the blisters. Turning the guide wheel 30 thus causes the blister strip to advance in a first direction. In a particular angular position, a given reservoir or blister is always in position to be opened by the opening means.

Figure 10:
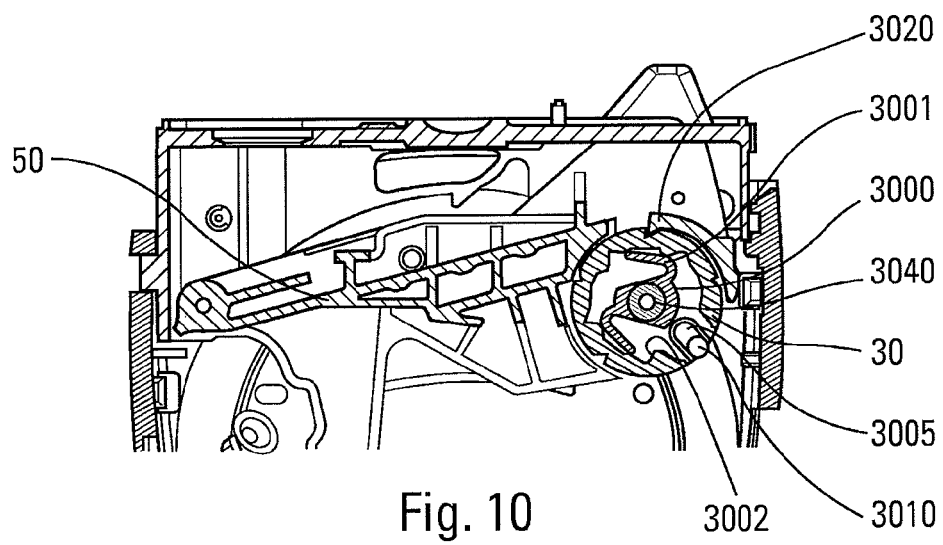
FIG. 10 is a diagram of still another variant of a fluid dispenser device, shown in its post-inhalation position.
Figure 11:
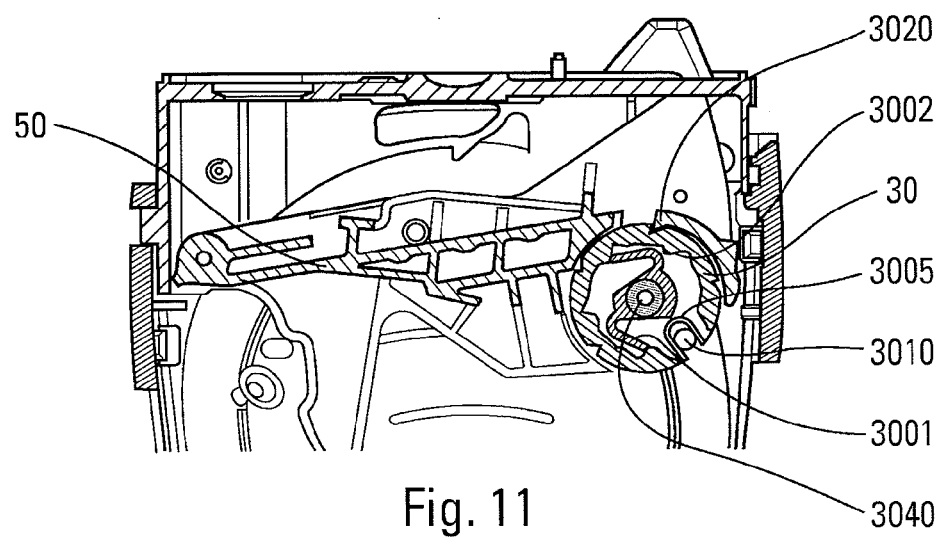
FIG. 11 is a view similar to the view in FIG. 10, shown after returning to its rest position.
Figure 12:
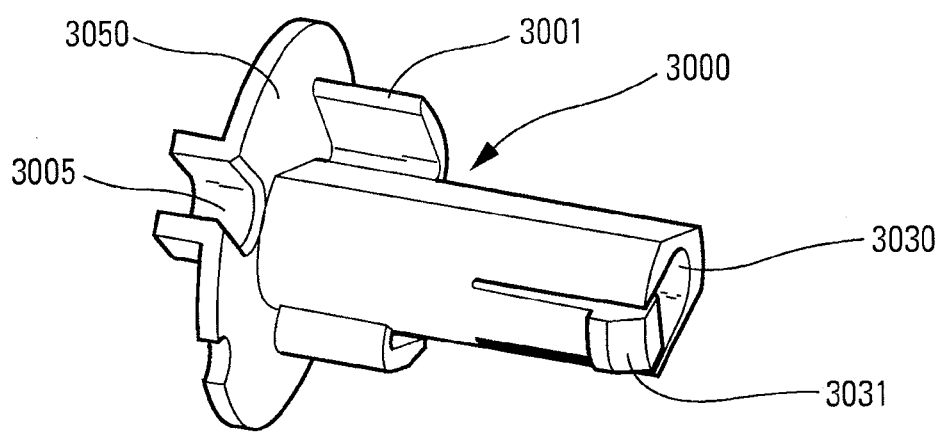
FIG. 12 is a diagrammatic perspective view of a detail in FIGS. 10 and 11.
Figure 13:
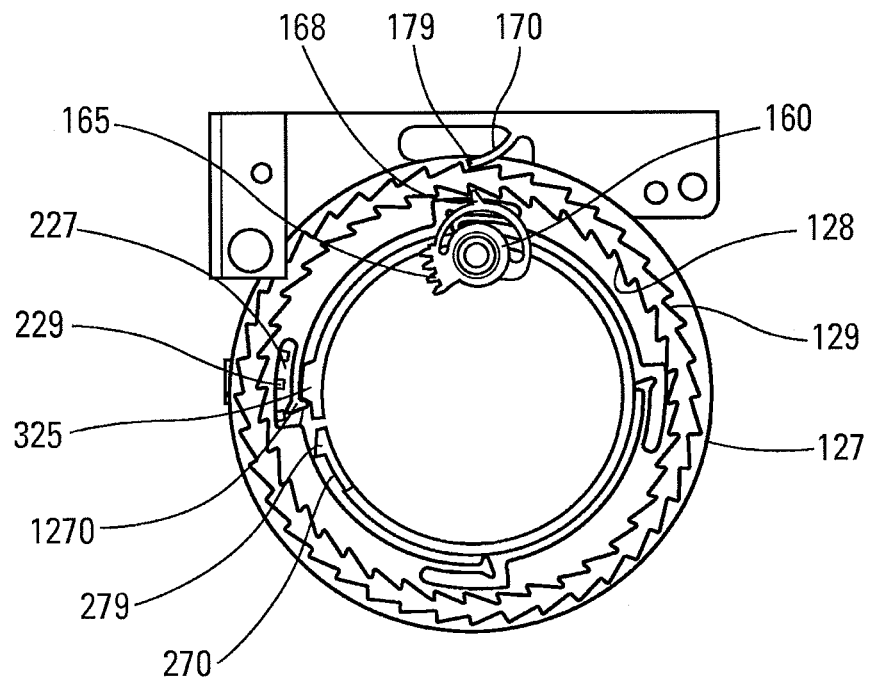
FIG. 13 is a diagrammatic section view of a portion of an advantageous counter, shown from behind.

The indexer wheel 30 thus forms first displacement means for displacing the reservoirs 21, making it possible to cause the flexible strip 20 to advance outside each actuation cycle, whereas said movable support means 50 form second displacement means that bring a respective reservoir against said opening means 80 on each actuation. FIGS. 10 to 12 show an advantageous variant for actuating said indexer wheel 30 so as to cause it to turn and thus cause the blister strip 20 to advance. In this variant, an actuator member 3000 is disposed in coaxial or concentric manner, radially to the inside of the indexer wheel. The actuator member 3000 is preferably rotatably mounted on a stud 3040 that is secured to the movable support means 50. The actuator means turns relative to the indexer wheel 30 and includes at least one and preferably two flexible tabs 3001 that are adapted to co-operate with an inner set of teeth 3002 of the indexer wheel 30. In a variant, the actuator member 3000 could include the set of teeth and the indexer wheel could include the flexible tab(s). In addition, the actuator member 3000 includes a groove 3005 that is adapted to co-operate with a portion of the body 10, e.g. a projection 3010 that is possibly flexible and/or deformable. Thus, when the movable support means 50 are displaced, causing the actuator member 3000 and the indexer wheel 30 to move therewith, the projection 3010 of the body, which remains stationary, causes the actuator member 3000 to turn in a first direction when the movable support means 50 return to their rest position, and in a second direction that is opposite to the first, when the movable support means 50 are displaced towards their dispensing position. Naturally, an inverse configuration can thus be envisaged. In said first direction, the flexible fingers 3001 push into the set of teeth 3002 so as to cause the indexer wheel 30 to turn, the anti-return means 3020 sliding over the slope with which they co-operate. In the second direction, the anti-return means 3020 prevent the indexer wheel 30 from turning, and the flexible tabs deformably slide over the sloping tabs of the teeth of the set of teeth 3002. The actuator member 3000 preferably includes a hollow central tube 3030 that is mounted on the stud 3040, and around which the indexer wheel 30 is assembled, preferably by snap-fastening on a snap-fastener tab 3031 of said tube. In addition, the actuator member 3000 advantageously includes an axial support plate 3050 that forms an axial abutment for the indexer wheel 30 that can thus turn on said actuator member, being held between said plate 3050 and said snap-fastener tab 3031.

Figure 2:
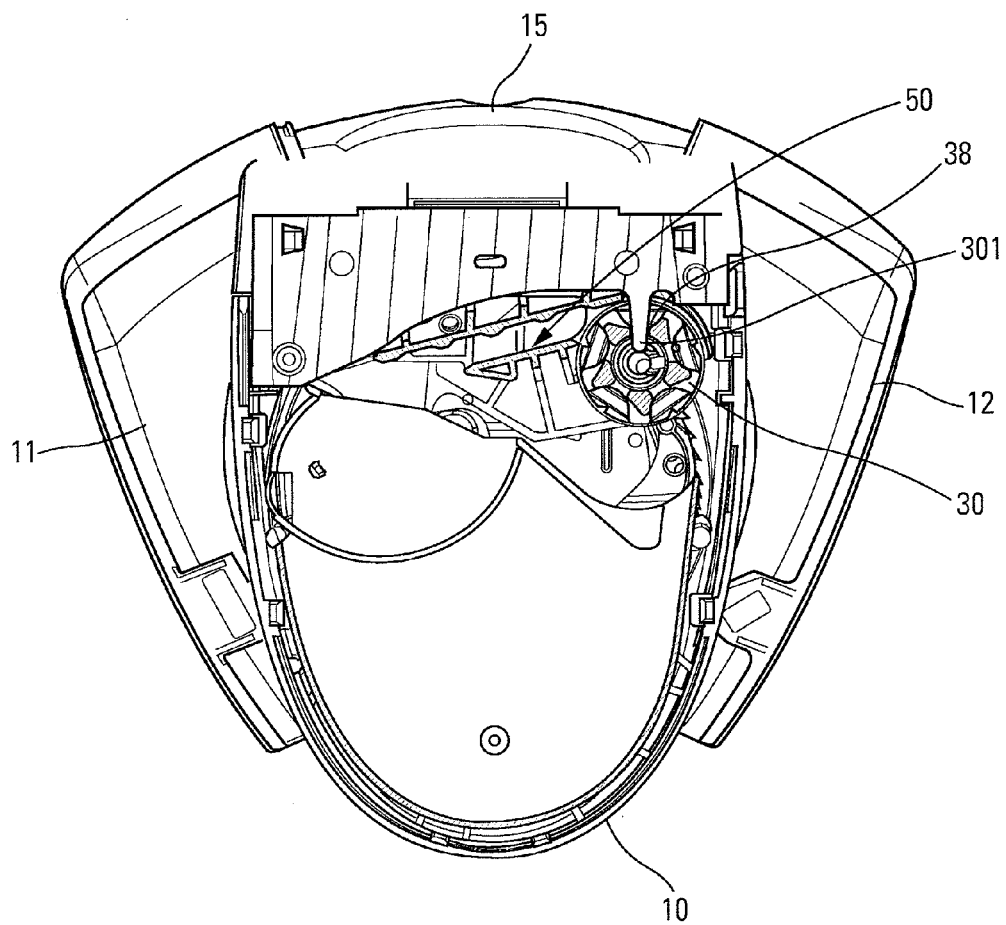
FIG. 2 is a view similar to the view in FIG. 1, shown in its post-inhalation position.

Advantageously, centering or positioning means 300 for centering or positioning said guide wheel 30 can be provided for accurately determining the angular position of said guide wheel 30 after each turn. In an advantageous variant, the positioning means 300 can comprise a projection or finger 301 having an end that co-operates with complementary reception means 38, such as notches, that are provided in said guide wheel 30. Advantageously, the finger 301 has an approximately V-shaped profile that automatically guides said finger 301 into the notch 38, thereby guaranteeing accurate angular positioning at each turn. The positioning means 300 are visible in FIGS. 1 and 2. The positioning means 300 can also determine the abutment position of the reservoir 21 relative to the opening means 80. Other abutment means can also be envisaged. An advantage of this type of abutment means is also to block the full reservoir abruptly just after it has been perforated by the needle 80, so as to shake the powder contained in the reservoir and also encourage it to be dispensed in the inhalation flow. Such abutment means could be used independently of the positioning means 300.

While the reservoir is being displaced towards its opening position in order to be opened by the opening means 80, the opening means are preferably stationary relative to the body 10. However, it is possible to envisage that the opening means could also move during the step of opening the reservoir. For example, the opening means could be displaced towards the reservoir while the reservoir is being displaced towards the opening means. In another variant, it is also possible to envisage that the reservoir and the opening means are displaced in the same direction during actuation, the reservoir being displaced more quickly in said direction, such that it comes into contact with said opening means in order to be opened.

As explained above, it is desirable for the opening means to be actuated by the user inhaling. In order to trigger the reservoir-opening means by inhalation, an inhalation trigger system is provided that advantageously comprises means 60 that are displaceable and/or deformable under the effect of inhalation, the means 60 being adapted to release the blocking means 100. The means 60 advantageously comprises a deformable air chamber 61 that co-operates with the blocking means 100 of said movable support means 50. Inhalation by the user causes said deformable air chamber 61 to deform, thereby making it possible to release said blocking means 100 and therefore unblock the movable support means 50, so as to make it possible to displace the guide wheel 30, and thus the reservoir to be emptied, towards its opening position. Advantageously, the air chamber 61 can comprise a deformable membrane 62, that can be connected firstly to the inhaler orifice 15, and secondly to said blocking means 100 in direct or indirect manner. Thus, during inhalation, the membrane 62 deforms and/or contracts, thereby causing said blocking means 100 to be displaced into an unblocking position. Advantageously, a pouch or diaphragm 62 can form the air chamber 61. The pouch 62 is connected to the inhaler orifice 15 via a channel 151 that is advantageously disposed around an expulsion channel 152 that is connected to a dispenser chamber 70. The pouch 62 may be fastened to a rod 101 that is connected to the blocking means 100, inhalation causing the pouch 62 to deform thereby causing the rod 101 to pivot in order to displace said blocking means 100. Advantageously, the pouch 62 can be made of silicone. In a variant, the deformable air chamber could be made in some other way, in particular by any deformable membrane.

Figure 5:
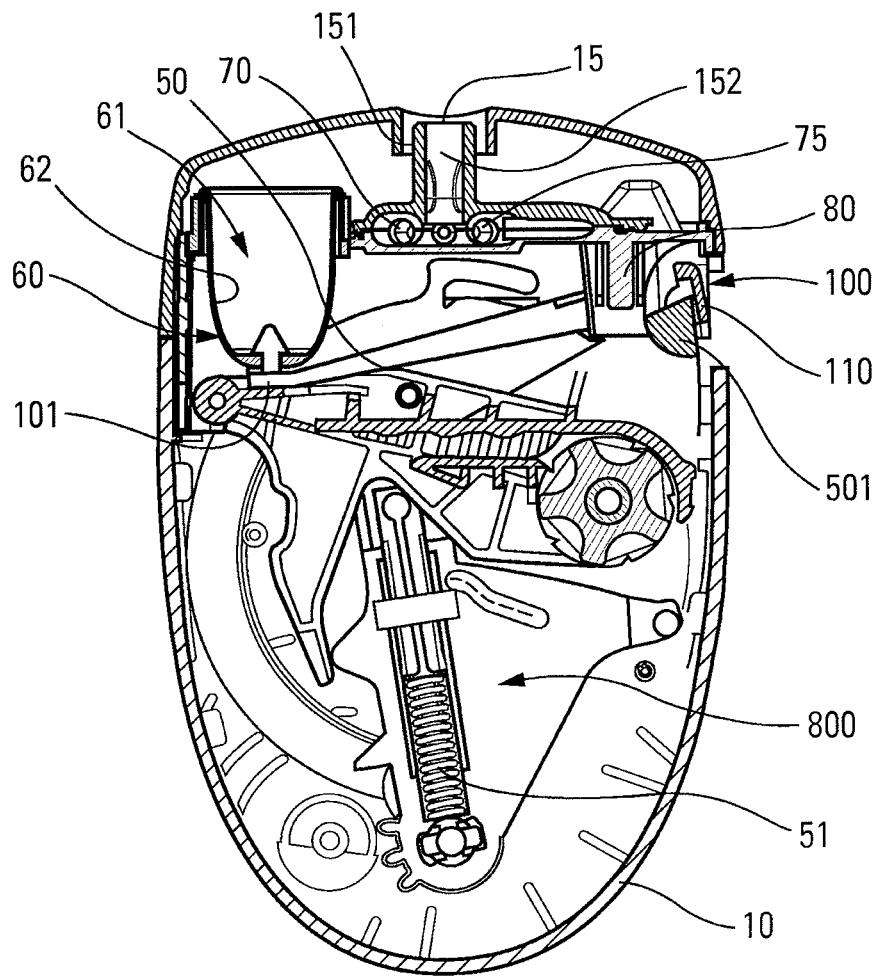
FIG. 5 is a diagrammatic view partially in section of still another variant of a fluid dispenser device, shown before being cocked.
Figure 6:
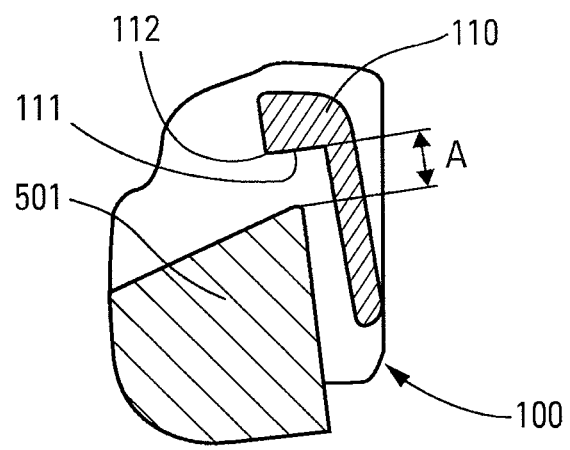
FIG. 6 is view of a detail in FIG. 5.

The inhaler further includes a dispenser chamber 70 for receiving the dose of powder after a respective reservoir has been opened. The dispenser chamber 70 is advantageously provided with at least one substantially spherical element 75, such as a bead, shown in FIG. 5, that is displaced inside said chamber 70 during inhalation so as to improve dispensing of the air and powder mixture after a reservoir has been opened, in order to increase the effectiveness of the device.

After inhalation, when the user closes the device, all of the components return to their initial, rest position, i.e. the movable support means 50 pivot about their pivot axis to return to their non-dispensing position by moving away from the reservoir-opening means, and the stressing element is also returned to its initial rest position in which it is not compressed or deformed. The device is thus ready for a new utilization cycle.

In a variant, other inhalation trigger means could also be used, e.g. using a pivotable valve flap that, while the user is inhaling, pivots under the effect of the suction created by the inhalation, with pivoting of the valve flap causing the blocking means blocking the movable support means to be released, thereby causing the reservoir to be displaced towards the opening means.

In another advantageous aspect of the inhaler, the individual reservoirs or blisters 21 are formed on an elongate strip 20 that is stored in the form of a roll inside the body 10 of the device. Advantageously, the rolled-up blister strip is held by inner walls of said body 10 without its "rear" end (rear in the displacement direction of the blister strip) being fastened relative to said body 10, thereby enabling the blister strip to be assembled more easily inside the device. The blister strip is advantageously displaced by means of the guide wheel 30 that advantageously presents at least one and preferably more recesses 31, shown in FIGS. 3 and 4, having a shape that corresponds substantially to the shape of the blisters. Thus, when the guide wheel 30 turns, it drives the blister strip in the first direction. Naturally, in a variant or in additional manner, it is possible to use other means for advancing the blister strip, e.g. providing a profile on the longitudinal lateral edges of the blister strip, said profile being adapted to co-operate with appropriate drive means. In addition, holes formed along the lateral edges of the blister strip could also be used to cause the blister strip to advance by means of toothed wheels co-operating with said holes, as with photographic film.

Advantageously, the leading end 25 of the blister strip 20 is fastened to a receiver element 500. To ensure that the leading portion of the blister strip 20, namely the portion including the empty blisters, is rolled up properly, the rotary receiver element 500 is adapted to exert a traction force on the strip 20, in particular on its leading end 25. Thus, any risk is avoided of the strip being rolled up poorly, e.g. folding up concertina-like, etc., which would risk blocking the device. The traction force can be exerted by a spring that urges said receiver element 500 to turn and thus pulls on the strip. In particular, the spring may be a spiral spring, a leaf spring, or a helical spring.

Figure 3:
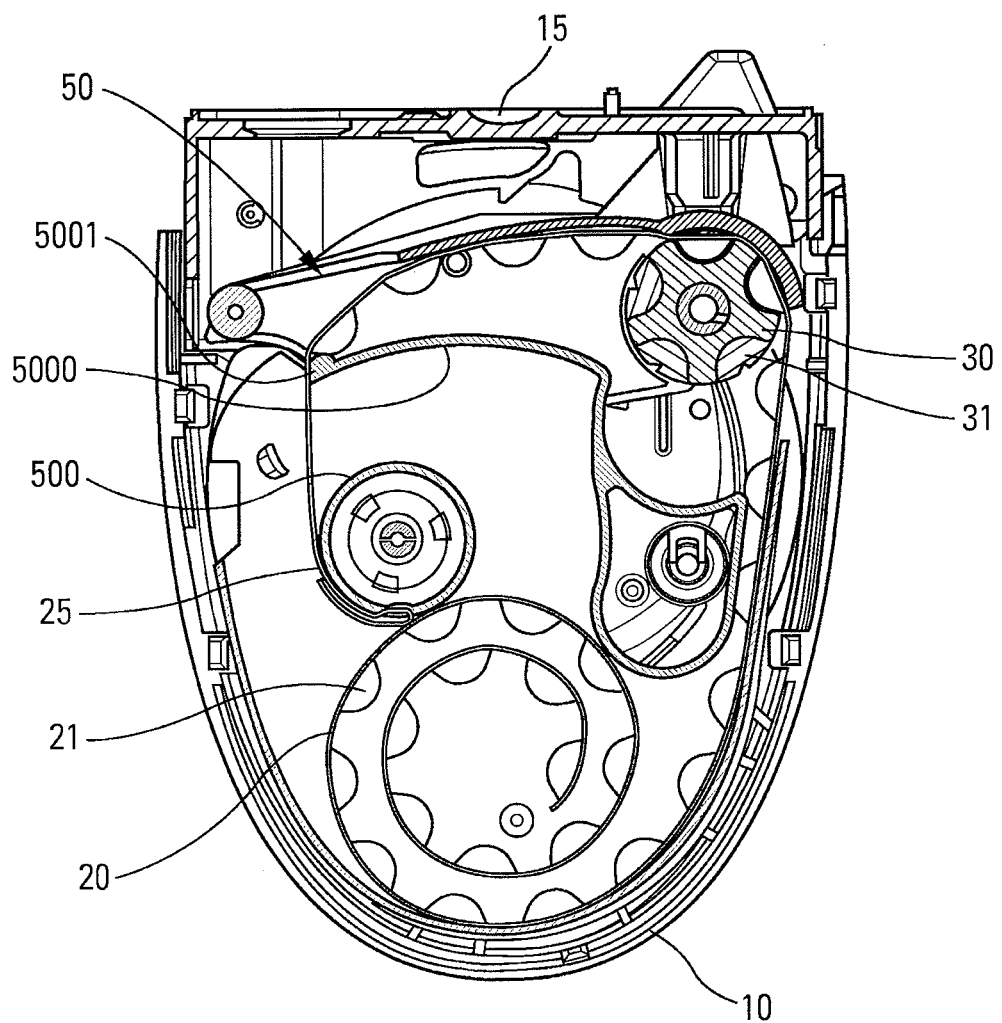
FIG. 3 is a diagrammatic view partially in section of another variant of a fluid dispenser device, shown in its post-inhalation position.
Figure 4:
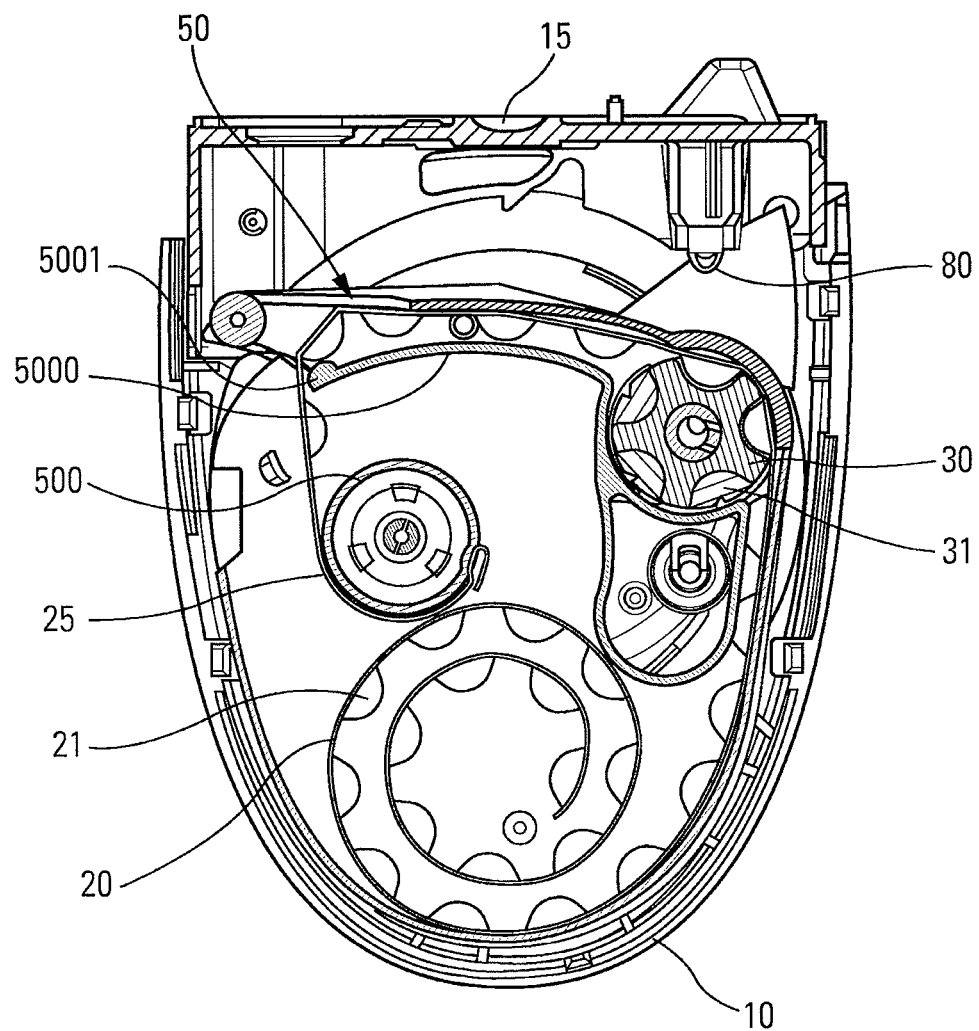
FIG. 4 is a view similar to the view in FIG. 3, shown in its cocked position, before inhalation.

FIGS. 3 and 4 show an advantageous variant embodiment, in which an abutment element 5000 is provided between the indexer wheel 30 and the receiver element 500. The purpose of the abutment element is to eliminate, or at the very least, to reduce the traction force exerted on the portion of the blister strip that is in contact with the indexer wheel 30. Such traction, if it is transmitted to said indexer wheel, could urge said wheel to turn, and thus prevent it from operating properly, e.g. causing it to be offset a little during actuation. Indexing, and also perforation of the blisters, could be affected thereby. With the abutment element 5000, the traction force is exerted by the receiver element 500 on the leading end 25 of the strip, but it is no longer applied (or it is applied at least to a lesser degree) on the strip portion disposed upstream of the abutment element 5000 in the direction of advancement of the strip 20. Advantageously, the abutment element co-operates, preferably via an end 5001, with an outer surface of each reservoir. As shown in FIGS. 3 and 4, the reservoirs or blisters are cavities each having a rounded outer surface, and the end 5001 of the abutment element 5000 is also preferably rounded. When the indexer wheel 30 is not turning, a reservoir is blocked by said end of the abutment element, and the strip thus cannot advance, nor exert traction on the indexer wheel 30. Conversely, when the indexer wheel is turned, it exerts thrust on the strip, which, combined with the traction exerted by the receiver element 500, makes it possible to go past the abutment and cause the blocked reservoir to pass over the abutment element so that the strip can advance. Advantageously, the blister strip forms an angle at the abutment element, the angle being greater when a reservoir (and thus also the indexer wheel 30) is displaced against the needle 80 FIG. 3). As the indexer wheel 30 turns while returning from the inhalation position (FIG. 3) to the rest position (FIG. 4), said turning begins with the greater angle, thereby making it easier for the blocked blister to pass over the abutment element 5000. Advantageously, the abutment element 5000 could be deformable or flexible, so as to make it even easier for the blister strip to advance during indexing.

The traction force exerted by the rotary element 500 on the strip 20 is completely independent of the first displacement means, namely the indexer wheel 30 that causes the strip to advance during each actuation. This makes it possible to guarantee that the traction force does not depend on the diameter of the rolled-up used blister strip, as would occur if the turning of the rotary receiver element 500 was correlated to the turning of the indexer wheel 30. The traction force is also completely independent of the second displacement means formed by the movable support means 50, such that the invention avoids providing actuator means that are relatively complex in order to create traction force on the strip during actuation of the inhaler. This simplifies the manufacture and assembly of the inhaler.

In still another aspect of the inhaler, a dose counter or indicator device is also provided. The device may include numbers or symbols that are marked directly on the blister strip, and that are visible through an appropriate window 19 in the body 10 of the device. In a variant, it is possible to envisage using a plurality of rotary disks including numbers or symbols, as described below.

Figure 7:
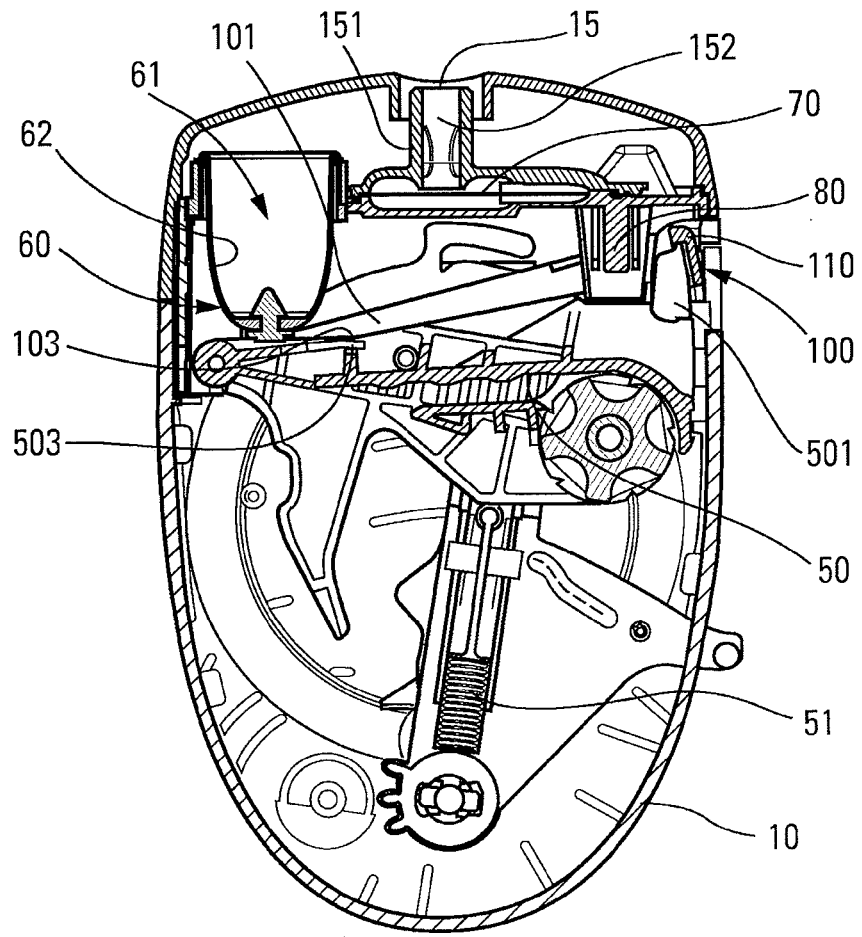
FIG. 7 is a view similar to the view in FIG. 5, shown after being cocked and before inhalation.

Blocking means 100 are provided for retaining said movable support means 50 in said non-dispensing position, corresponding to a stressed blocking position of the blocking means shown in particular in FIG. 7. Said blocking means 100 advantageously include a blocking element 110 that is adapted to co-operate with said extension or projection 501 of said movable support means 50. Said blocking element 110 includes a bearing surface 111 that is substantially plane and that co-operates with the projection 501, preferably of rounded shape, so that said projection slides over said bearing surface when the blocking element pivots towards its unblocking position. When the projection arrives at an end edge 112 of the bearing surface, it is no longer retained, and the movable support means 50 can be displaced towards their dispensing position under the effect of the force exerted thereon by the stressing means 800. Said blocking means 100 are advantageously connected by means of a rod 101 to the deformable diaphragm 62 that is sensitive to inhalation by the user, so that while the user inhales, said diaphragm deforms, thus causing the rod 101 to pivot, and consequently said blocking element 110, thereby releasing the extension 501. This enables said movable support means 50 to be displaced towards their dispensing position under the effect of the force exerted by the compressed spring 51. The displacement of the movable support means 50 causes an individual reservoir to be opened, as described above.

In the stressed blocking position, shown in FIG. 7, the movable support means 50 that are urged towards the dispensing position by the compressed spring 51 thus exert a force on the blocking means 100, in particular on the blocking element 110 of the blocking means, by means of the extension 501. At the opposite end of the rod 101, in the proximity of the connection of said rod 101 to the diaphragm 62, a bearing zone 103 is advantageously provided, adapted to co-operate with a complementary zone 503 provided on the movable support means 50. The bearing zone 103 makes it possible to create a stressed position that is stable between said movable support means 50 and said blocking means 100. Each of the two means are movable, and the dual contact, firstly with a force exerted upwards (with reference to the position shown in FIG. 7) by the extension 501 on the shoulder portion 110, and secondly with a force exerted downwards by the bearing zone 103 on the complementary zone 503, guarantees balanced blocking that can be released only by the user inhaling, causing the diaphragm 62 to deform, and thus the rod 101 of the blocking means 100 to pivot.

Figure 9:
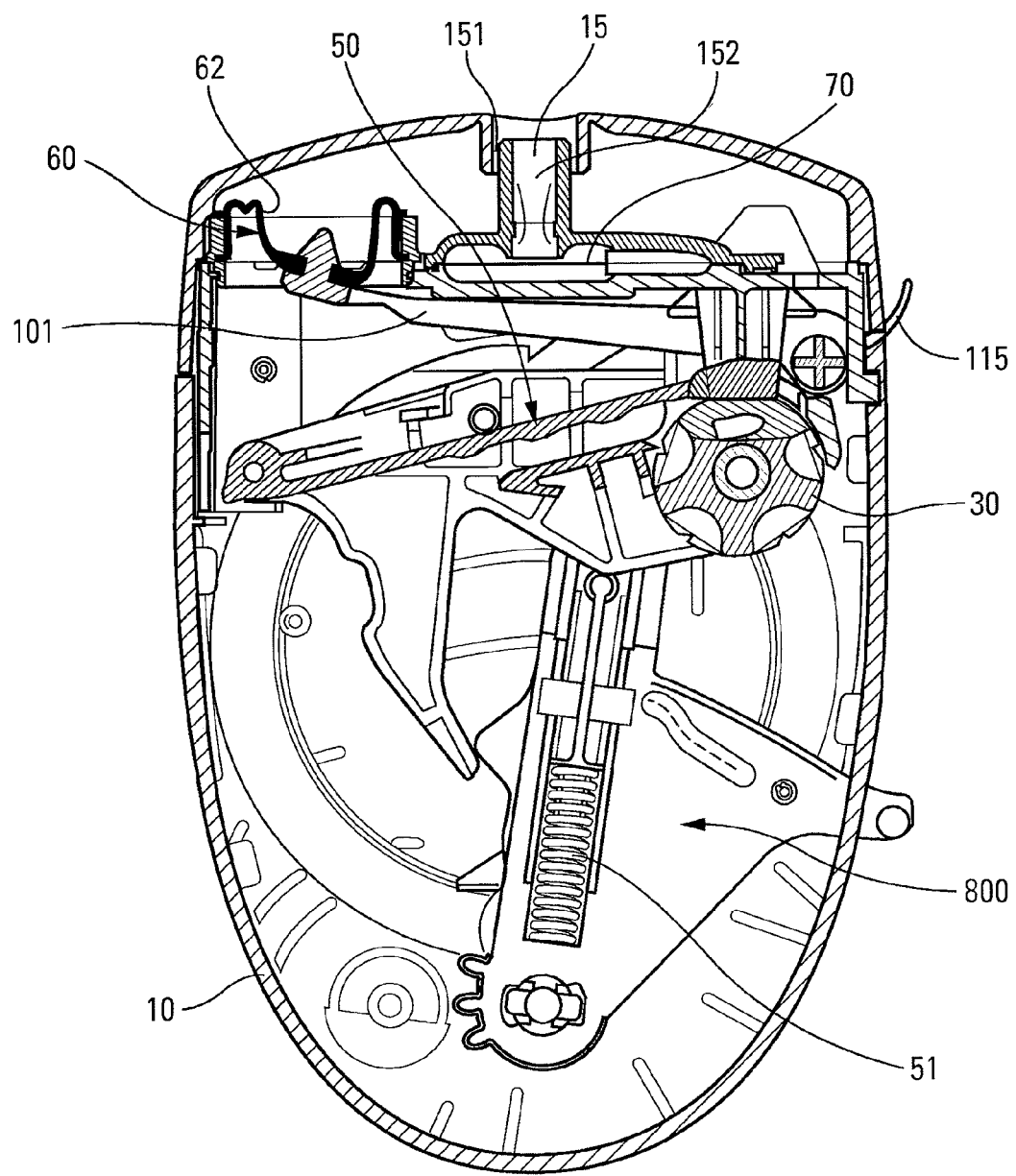
FIG. 9 is a view similar to the view in FIGS. 5 and 7, shown after inhalation.

After inhalation, i.e. in the dispensing position shown in FIG. 9, the blocking means 100 have pivoted, and the movable support means 50 have been displaced upwards by the compressed spring 51. The pivoting of the blocking means, in particular of the blocking element 110, may cause an end portion 115 of the blocking element 110 to project out from the body 10, as shown in particular in FIG. 9. Then, when the user closes the movable cover elements, one of the cover elements, when fully closed, comes to bear against said end portion 115, thereby returning the blocking means 100 to their initial position with the diaphragm 62 that is also returned to its initial position, as shown in particular in FIG. 5.

Thus, by opening the inhaler, the user stresses the system. If the user does not inhale and closes the inhaler, said inhaler merely returns to its start position without displacing the reservoirs 21 or the blocking means 100. There is thus no risk of a reservoir (and thus an active dose of substance) being lost by accidental or incomplete actuation in which the user does not inhale between opening and closing. Opening the reservoir, emptying it, dispensing the powder into the lungs of the user, and displacing the blister strip to bring a new full reservoir to face the opening means is thus possible only if the user inhales.

Thus, the blocking means need to be put under stress in order to be released. Prestressing is thus applied to the mechanism. The patient's inhalation causes the deformable element (diaphragm) 62 to deform, thereby causing the blocking element 110 to turn and the mechanism to be released. An advantage of the blocking means is to be able to function with a ratio of 100 between applied prestressing and the force necessary to deform the diaphragm. A force in the range 0.05 newtons (N) to 0.2 N is generally sufficient to deform the diaphragm (which force is generated by patient inhaling) in spite of a prestressing force in the range 5 N to 10 N being applied to the mechanism (prestressing making it possible to guarantee a perforation force that is sufficient to enable the needle to penetrate into the blister 21). It suffices for the patient to generate a pressure difference lying in the range 4 millibars (mbar) to 15 mbar (pressure corresponding to inhalation at a rate lying in the range 10 liters per minute to 20 liters per minute) in order to trigger the mechanism: this inhalation rate is a rate that is considered to be comfortable for a patient who is asthmatic or who has a chronic respiratory tract disease. The rate being generated at the end of perforation enables the powder to be guided towards the patient's bronchi, while if the minimum inhalation rate is not achieved then no dose is released: this prevention device thus prevents the fluid dispenser device from being triggered accidentally.

Judicious sharing of the air flow makes it possible to guarantee the operation of the blocking means (½ to ⅔ of the overall flow), while also achieving the desired powder-dispensing performance (⅓ to ½ of the overall flow).

Figure 8:
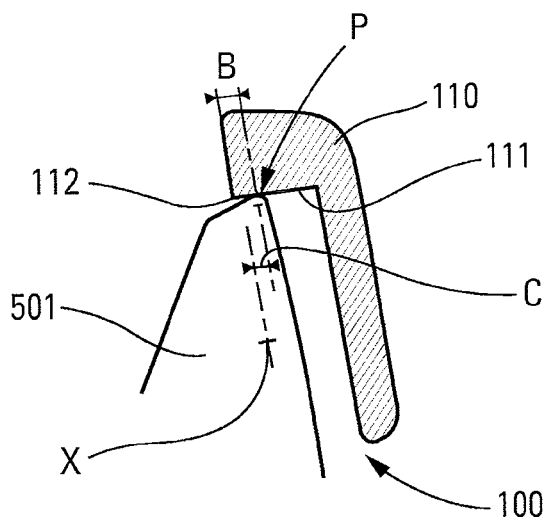
FIG. 8 is view of a detail in FIG. 7.

In order to ensure the blocking means 100 are stable, an engagement value C (see FIG. 8) is provided in order to guarantee that the prestressed blocking means are held sufficiently firmly to withstand vibration and impacts. Accidental triggering that is not desired and not triggered by the user should be avoided. The engagement value C corresponds to the distance between the projection of the prestressing force exerted on the blocking element 110 at the point of contact P between the projection 501 with the bearing surface 111, and the axis of rotation X of the blocking element 110. The engagement C has a non-zero value that is less than 0.5 millimeters (mm), and advantageously lies in the range 0.2 mm to 0.4 mm. The engagement C is coupled to abutments 103, 503 that hold the prestressed mechanism in a stable equilibrium position. The energy stored in this way is released during perforation, after inhalation. The purpose of the abutments is also to avoid blocking the lock (during an impact or resulting from vibration): the trigger point thus remains identical whatever the conditions of use of the device. A guard value B (see FIG. 8) makes it possible to provide trigger synchronization in the inhalation cycle, so as to guarantee good trigger timing, in order to maintain a sufficient volume of air to expel and break up the dose. It also makes it possible to adjust the trigger instant as a function of patients' inhalation profiles. The guard value B corresponds to a non-zero distance (less than 0.5 mm, advantageously about 0.2 mm) between the point of contact P between the projection 501 with the bearing surface 111, and the end edge 112 thereof, as shown in FIG. 8.

The blocking means can be re-cocked by a lever 115 (FIG. 9), or, in a variant, by a torsion spring, or even by the resilience of the diaphragm 62. Such re-cocking enables the mechanism to return to its initial state after each inhalation cycle as soon as the inhaler is closed, and in repeatable manner.

In advantageous manner, in the event of the device being opened and closed without any inhalation, the system remains at rest. There is therefore no risk of overdosing. In addition, no prestress is applied while the inhaler is not open, thereby favoring the stability of the components over time. Advantageously, when the inhaler is in the closed position, the projection 501 is disposed at a non-zero distance A from the bearing surface 111 so as to ensure the system can be re-cocked.

Figure 14:
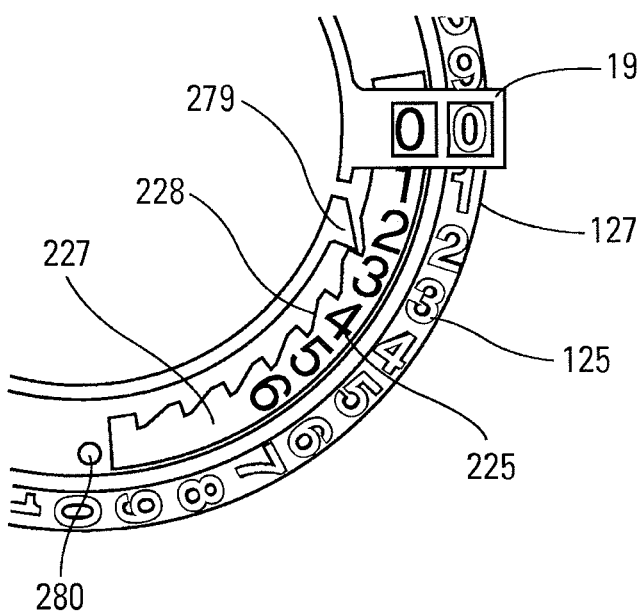
FIG. 14 is a fragmentary section view of the counter portion in FIG. 13, shown from the front.
Figure 15:
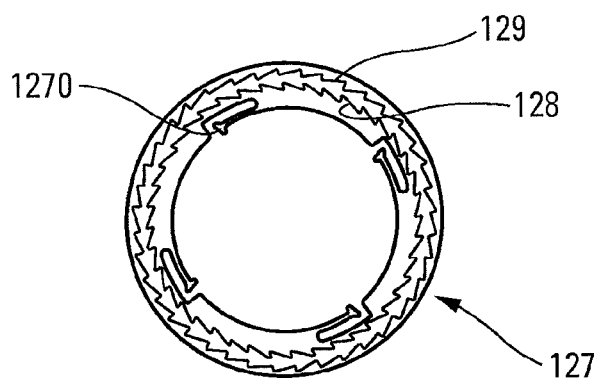
FIGS. 15 and 16 are rear and front views respectively of the first rotary counter element.
Figure 16:
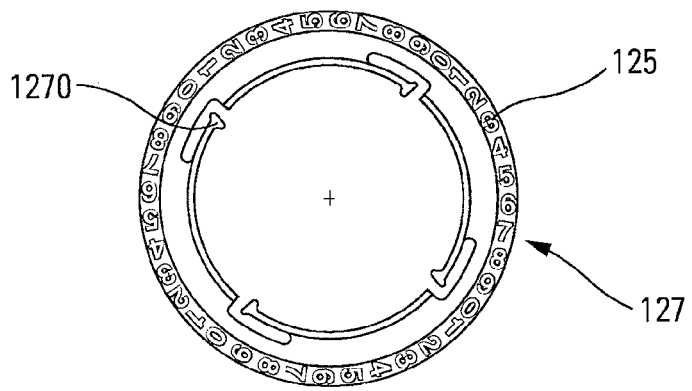
Figures 17A, 17B:
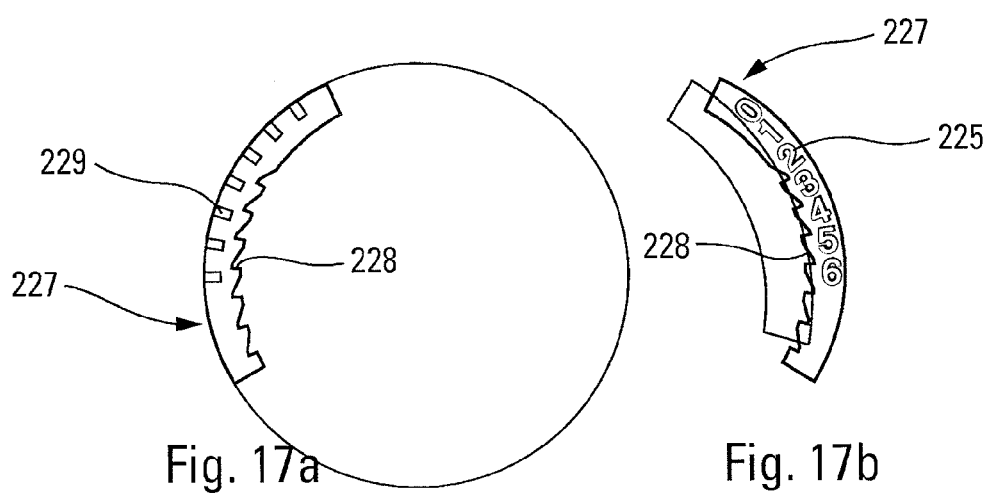
FIGS. 17a and 17b are rear and front fragmentary views respectively of the second rotary counter element.
Figure 20:
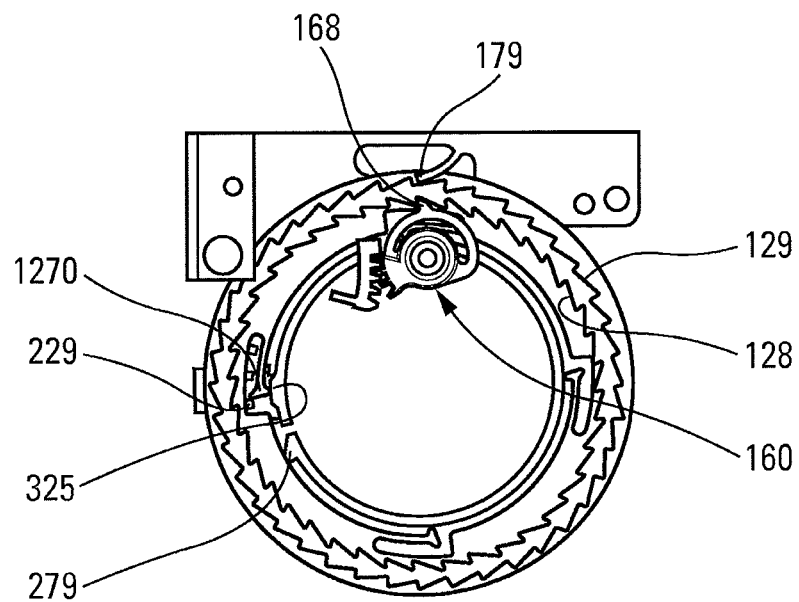
FIG. 20 is a diagrammatic section view similar to the view in FIG. 13, with the deformable finger deformed by the cam.
Figure 21:
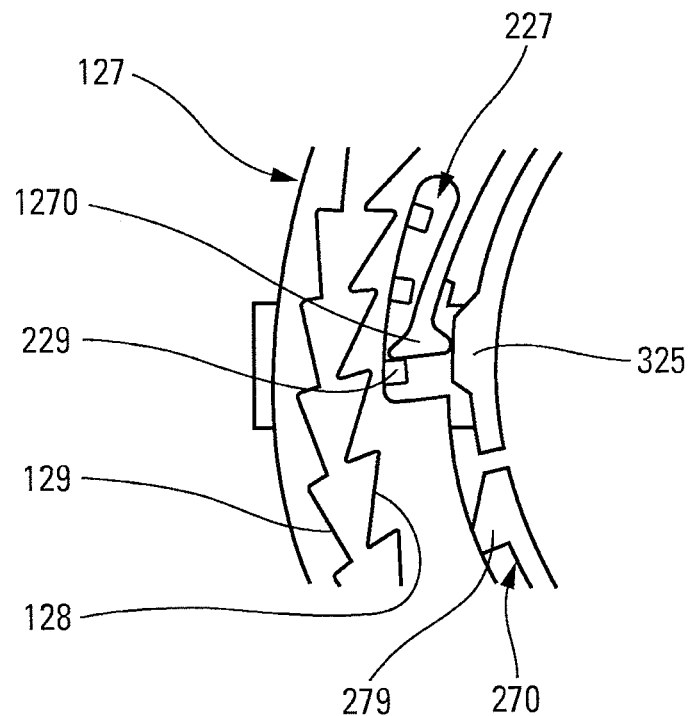
FIG. 21 is view of a detail in FIG. 20.

The device of the invention includes a dose indicator or counter that is adapted to count or indicate to the user the number of doses that have been dispensed or that remain to be dispensed. In the embodiment shown, the indicator is adapted to count 60 doses. The indicator includes at least two rotary counter elements, a first counter element for counting units 127, and a second counter element for counting tens 227. The first counter element is advantageously a first ring 127 provided with an inner set of teeth (first set of teeth) 128 and with an outer set of teeth (second set of teeth) 129 and including indicator means 125, e.g. numbers from 0 to 9, provided on one of its surfaces. Preferably, the indicator means 125 are disposed on a top surface, whereas the sets of teeth are disposed on a bottom surface. The inner set of teeth 128 is advantageously adapted to co-operate with an actuator element or an actuator 160, whereas the outer set of teeth 129 is advantageously adapted to co-operate with first anti-return means 170 that are adapted to prevent the first ring 127 from turning in the opposite direction to the direction that is imposed thereto by the actuator 160. The first ring 127 includes at least one deformable finger 1270, preferably four fingers that are distributed at 90° intervals around its periphery, the deformable finger(s) being adapted to co-operate every ten actuations with a cam 325 that is secured to the body. The second counter element is advantageously a second ring, preferably, as shown in FIGS. 17a and 17b, a portion of an angular section of second ring 227, in particular a section of 90° or less. This embodiment is advantageous since it is compact. The second ring 227 includes a first set of teeth 228 and a second set of teeth 229, and second indicator means 225 on one of its surfaces. For a 60-dose counter, the second indicator means can include the digits 0 to 6, for example. Preferably, the second ring 227 is coaxial with the first ring 127, the surfaces including the indicator means 125, 225 being coplanar, the second ring 227 being radially inside the first ring 127. In this way, the first and second indicator means 125, 225 may be displayed simultaneously in an appropriate viewing window 19, as shown in FIG. 14. The set of teeth 229 of the second ring 227 is for co-operating with the deformable finger 1270 of the first ring each time it is displaced towards its deformed position by said cam 325, as shown in FIGS. 20 and 21. When it is not deformed, said finger 1270 does not co-operate with said second set of teeth 229. Thus, in the embodiment shown in the drawings, the first ring includes four deformable fingers 1270, and four series of digits 0 to 9 distributed over the periphery, the sets of teeth 128, 129 including forty teeth. On each actuation, the first ring 127 thus turns through 9°, which corresponds to the advance of one number in the window 19. Every ten actuations, a deformable finger 1270 co-operates with said cam 325, preferably provided radially inside said finger, so as to deform outwards and thus co-operate with the second set of teeth of the second ring. The second ring 227 is thus also turned through an angle of 9°. The first set of teeth 228 of the second ring is for co-operating with second anti-return means 270, e.g. a second flexible tab 279 that can be secured to the body. It should be observed that the first and second anti-return means 170, 270 could also co-operate with the same sets of teeth as the actuator 160 and the deformable finger 1270, in which event the first and second rings 127, 227 could each include only a single set of teeth. When the second counter element is an angular ring section as shown in the drawings, its first and second sets of teeth can include only the number of teeth that is necessary, i.e. seven teeth for a 60-dose counter (corresponding to the digits 0 to 6). Naturally, the number of deformable fingers 1270 and the number of series of digits 0 to 9 on the first ring could be different, as a function of requirements.

Figure 18:
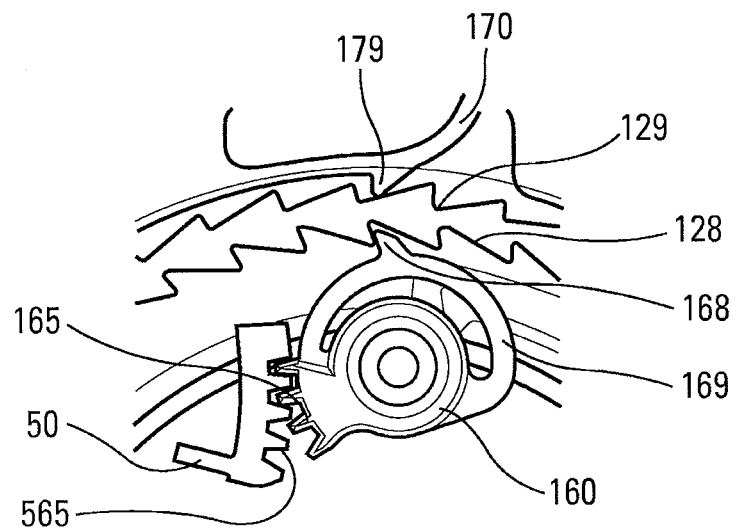
FIGS. 18 and 19 are fragmentary views of the actuator element, shown in its rest and actuated position respectively.
Figure 19:
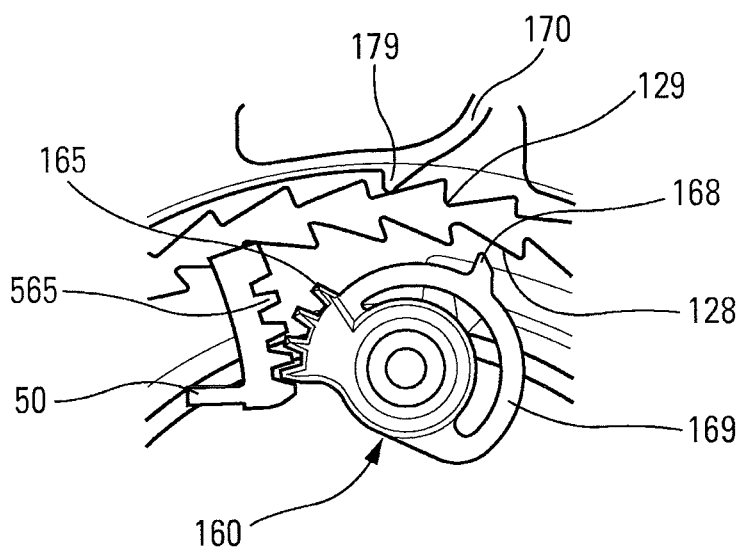

An object of the invention is to avoid counting doses that have not been dispensed, e.g. in the event of a manipulation error, or of an incomplete manipulation of the device. It is thus essential that the counter or indicator is actuated only once the user has inhaled, since it is this inhalation that makes it possible for the blister to open and the dose contained therein to be dispensed. To do this, the device includes an actuator or actuator element 160 that is pivotally mounted on the body 10 to pivot between a first position and a second position. The actuator 160 includes engagement means 165, in particular a first set of teeth 165, adapted to mesh in a second set of teeth 565 (or complementary teeth) provided on movable support means 50. Thus, when the user opens the device and stresses the stressing means of the device, the movable support means 50 do not move since they are held in the non-dispensing position by the blocking means 100. Thus, nothing happens to the indicator since the actuator 160 that is pivotally mounted on the body 10 and meshed with the movable support means 50, also remains stationary. If the user closes the device without inhaling, obviously still nothing happens since the movable support means 50 still remain stationary. In this way, it is guaranteed that the indicator does not count doses if there is no inhalation. From the stressed position, if the user inhales, the movable support means 50 are displaced into their dispensing position towards the opening means. This displacement thus causes the actuator 160 to pivot in a first direction, as shown in FIGS. 18 and 19. The actuator 160 includes a finger 168 that is meshed in the inner set of teeth 128 of the first indicator ring 127. In the first displacement direction, the finger 168 of the actuator can slide over the slope of the corresponding tooth so as to become positioned facing the next tooth. In parallel, the anti-return means 170, in particular an anti-return finger 179, co-operate with the outer set of teeth 129 of the ring 127 so as to prevent said ring from turning under the effect of friction, e.g. exerted by the finger 168 of the actuator on the inner set of teeth 128. After inhalation, when the user closes the device, the movable support means 50 are returned to their rest position, i.e. the non-dispensing position. This movement thus causes the actuator 160 to pivot in the direction opposite to the first-described direction, since the respective sets of teeth 165, 565 of the actuator and of the movable support means pivot in the direction opposite to the above-described direction. In the displacement in the opposite direction, the finger 168 of the actuator 160 presses into the tooth in which it is positioned so as to cause the first ring 127 to turn, as shown in FIG. 18. In parallel, the anti-return finger 179 slides over the slope of the tooth so as to become positioned in the following tooth of the outer set of teeth 129. In a variant, the first ring 127 could be turned while the movable support means 50 are being displaced towards their dispensing position, e.g. reversing the direction of the teeth of the first set of teeth of the first ring 127.

An advantage of the counter of the present invention is that it makes a large display possible without increasing the size of the counter and thus of the inhaler. In particular, the embodiment shown makes it possible, for a 60-dose counter, to display numbers (firstly units, secondly tens) having a height that is greater than 2.5 mm, preferably about 2.8 mm, and a width that is greater than 1.5 mm, preferably about 2.1 mm. This represents an increase in the size for the numbers of up to 50% compared to existing counters.

In the embodiment shown, the indicator is adapted to indicate the number of doses that remain to be dispensed, so that the number displayed decreases on each actuation. Naturally, the opposite is also possible, i.e. a counter that counts the number of doses that have been dispensed. Advantageously, it is possible to provide blocking means for blocking the indicator after the last dose has been dispensed. The blocking means can take different forms, an advantageous form being to provide a tooth of different shape on the inner set of teeth of the first ring 127 so that the actuator can no longer become meshed in the next tooth in order to continue causing said first indicator ring to turn. Other means for preventing the first ring from turning after the last dose has been dispensed can also be envisaged. For example, an abutment 280 for the second tens ring 227, as shown diagrammatically in FIG. 14.

In all of the embodiments described above, the blister strip is formed by a strip presenting two ends. In a variant, it is possible to use a continuous strip. Other modifications are also possible without going beyond the ambit of the present invention.

The present invention therefore makes it possible to provide a dry-powder inhaler that performs the following functions:

a plurality of individual doses of powder stored in individual sealed reservoirs, e.g. 30 or 60 doses stored on a rolled-up strip;

the powder is released by perforation that is achieved by the user inhaling, the blister being perforated by means of an inhalation detector system that is coupled to a prestressed release system;

appropriately-shaped drive means that are engaged with blisters so as to displace the blister strip on each actuation, and to bring a new reservoir into a position in which it is to be opened by appropriate opening means;

means for avoiding doses being lost in the event of the inhaler being opened, but in the absence of any inhalation. In this event, when the inhaler closes, the device returns exactly to its start position; and a dose indicator adapted to count the doses only in the event of inhalation.

Other functions are also provided by the device of the invention as described above. It should be observed that the various functions, even if they are shown as being provided simultaneously on the various embodiments of the inhaler, could be implemented separately. In particular, the inhalation trigger mechanism could be used regardless of the type of reservoir-opening means, regardless of the use of a dose indicator, regardless of the way in which the individual reservoirs are arranged relative to one another, etc. The cocking means and the inhalation trigger system could be made in some other way. The same applies for other component parts of the device.

The inhaler of the invention, incorporating all or some of the above-described functions, provides performance that is superior to the performance of existing devices. In particular, the inhaler of the invention preferably provides a reservoir emptying factor of at least 90% on each actuation. The emptying factor, corresponding to the percentage of fluid that is expelled from an open reservoir while the device is being actuated, is advantageously greater than 95%, preferably even greater than 97%. In particular, this high emptying factor is even greater than the performance obtained with active inhalers that are generally more effective than passive inhalers, and in which it is not the inhalation flow that empties the blister and expels the dose but a flow of compressed air that is released while inhaling. The high emptying factor guarantees that the device of the invention is as effective as possible. Coupled with the inhalation-triggered opening, the high emptying factor guarantees that the fluid, specifically the powder, is dispensed in optimum manner into the user's lungs. The invention also provides improved emptying regularity of the reservoirs during successive actuations. Thus, for ten reservoirs of a blister strip, for example, it turns out that the emptying factor varies by less than 15%, advantageously by less than 10%, preferably by less than 5% from one reservoir to another. This improved regularity guarantees improved dose reproducibility, and therefore also improved effectiveness of the device of the invention.

Various modifications can also be envisaged by a person skilled in the art, without going beyond the ambit of the present invention, as defined by the accompanying claims. In particular, the various characteristics and functions of the device described with reference to the various embodiments and variants can be adapted to all of the embodiments and variants, and can be combined together in any appropriate manner.

The invention claimed is:

1. A fluid dispenser device comprising: a body provided with a dispenser orifice; a plurality of individual reservoirs each containing a dose of powder; dispenser means for dispensing a dose of fluid on each actuation, said dispenser means including reservoir-opening means comprising a reservoir-perforator element that is stationary relative to the body, and reservoir displacement means for displacing a full reservoir against said perforator element, thereby opening it and releasing the dose of powder, said reservoir displacement means being controlled by the user inhaling; and a dose counter for indicating the number of doses that have been dispensed or that remain to be dispensed, and said counter comprises:
a first rotary counter element provided with a first surface including first indicator means, such as digits, and provided with at least one first set of teeth;
a second rotary counter element provided with a second surface including second indicator means, such as digits, and provided with at least one second set of teeth; and
a movable actuator element that is displaceable between a first position and a second position, said actuator element including a projection that is adapted to co-operate with said first set of teeth of said first counter element, so as to cause said first counter element to turn while said actuator element is being displaced from its first position to its second position, said actuator element being rotatably mounted on the body, turning in a first direction bringing the projection to push a tooth of said first set of teeth of the first counter element so as to cause said first counter element to turn, and turning in the opposite direction bringing the projection to slide over said tooth so as to engage in the following tooth without causing said first counter element to turn;
said first counter element including at least one deformable finger that is displaceable between a non-deformed position and a deformed position, and that is adapted to co-operate, in its deformed position, with said second set of teeth of said second counter element, so as to cause said second counter element to turn;
said body including a cam that is adapted to deform said at least one deformable finger toward its deformed position; and
said reservoir displacement means co-operating with said actuator element of the counter, such that when said reservoir displacement means displace a reservoir against or away from the perforator element, the actuator element causes said first counter element to turn,
wherein said second indicator means comprise digits that form the tens of the counter, said second indicator means comprising digits from 0 to 6 disposed over a peripheral portion of said second counter element,
wherein said second rotary counter element is formed as an angular ring section having two ends, wherein the two ends are no more than 90° apart from each other.

2. A device according to claim 1, wherein said first set of teeth of the first counter element comprises forty teeth, each actuation of the counter causing said first counter element to turn through an angle of 9.

3. A device according to claim 1, wherein said second set of teeth of said second counter element comprises at least seven teeth, and each time said cam deforms the deformable finger towards its deformed position, said second counter element is caused to turn through an angle of 9°.

4. A device according to claim 1, wherein said second surface of said second counter element is coplanar with, and radially inside, said first surface of said first counter element, said first and second counter elements being concentric.

5. A device according to claim 1, wherein said body includes a viewing window in which first and second indicator means are displayed simultaneously.

6. A device according to claim 1, wherein the counter includes abutment means that prevent any additional actuation after the last dose has been counted.

7. A device according to claim 1, wherein said projection is secured to a deformable branch of said actuator element.

8. A device according to claim 1, wherein said actuator element includes a first gear that co-operates with a second gear that is secured to a movable member that is displaced when the user inhales.

9. A device according to claim 1, wherein said first indicator means comprise digits 0 to 9 that form the units of the counter.

10. A device according to claim 9, wherein said first indicator means comprise four series of digits 0 to 9 that are distributed over the periphery of said first counter element.

11. A device according to claim 1, wherein said first and second indicator means are digits having a height that is greater than or equal to 2.5 millimeters (mm).

12. A device according to claim 11, wherein the height of the digits is 2.8 mm.

13. A device according to claim 1, wherein said first and second indicator means are digits having a width that is greater than or equal to 1.5 mm.

14. A device according to claim 13, wherein the width of the digits is 2.1 mm.

15. A device according to claim 1, wherein said first rotary counter element includes four deformable fingers that are disposed regularly around a periphery of said first counter element.

16. A device according to claim 15, wherein said first counter element is a first ring including a radially-outer periphery and a radially-inner periphery, said deformable fingers being disposed at 90° from one another on said radially-inner periphery, and co-operating with a cam that is disposed radially inside said first ring, such that when a deformable finger co operates with said cam, it is deformed radially outwards into its deformed position, so as to become engaged with said second set of teeth of said second counter element.

17. A device according to claim 1, wherein first anti-return means are provided so as to prevent said first counter element from turning in the direction opposite to the direction imparted thereto by said actuator member.

18. A device according to claim 17, wherein said first anti-return means include at least one flexible tab that co-operates with a set of teeth, in particular a second set of teeth, of said first indicator element.

19. A device according to claim 1, wherein second anti-return means are provided so as to prevent said second counter element from turning in the direction opposite to the direction imparted thereto by said at least one deformable finger.

20. A device according to claim 19, wherein said second anti-return means include at least one second flexible tab that co-operates with a set of teeth, in particular a first set of teeth, of said second indicator element.

* * * * *